(12) United States Patent
Shieh et al.

(10) Patent No.: US 6,377,851 B1
(45) Date of Patent: Apr. 23, 2002

(54) IMPLANTABLE CARDIAC STIMULATION DEVICE AND METHOD FOR OPTIMIZING SENSING PERFORMANCE DURING RATE ADAPTIVE BRADYCARDIA PACING

(75) Inventors: Mae-Mae Shieh, Fontainebleau (FR); Jim C. Chen, New York, NY (US); Anthony Mo, Fremont; Eric S. Fain, Menlo Park, both of CA (US)

(73) Assignee: Pacesetter, Inc.

( * ) Notice: Subject to any disclaimer, the term of this patent is extended or adjusted under 35 U.S.C. 154(b) by 0 days.

(21) Appl. No.: 09/484,868

(22) Filed: Jan. 18, 2000

Related U.S. Application Data
(60) Provisional application No. 60/172,389, filed on Dec. 17, 1999.

(51) Int. Cl.$^7$ ............................................. A61N 1/362
(52) U.S. Cl. ............................................................ 607/9
(58) Field of Search .................................... 607/4, 5, 9

(56) References Cited

U.S. PATENT DOCUMENTS 5,129,393 A   7/1992  Brumwell
5,269,300 A  12/1993  Kelly et al. ..................... 607/4
5,395,393 A   3/1995  Wickham ........................ 607/5
5,560,369 A  10/1996  McClure et al.
5,709,215 A   1/1998  Perttu et al.

OTHER PUBLICATIONS

Medtronic GEM DR Dual Chamber ICD System, Model 7271, The Logical Choice; Medtronic 1998, 4 pages.

Primary Examiner—Scott M. Getzow
(74) Attorney, Agent, or Firm—Steven M. Mitchell

(57) ABSTRACT

An implantable cardiac stimulation device including a ventricular defibrillator and a rate adaptive cardiac pacer automatically adjusts post-pacing sensing parameters dependent upon pacing rate. The device includes a pulse generator that applies stimulation pulses to a heart at a calculated variable stimulation rate as a function of physiologic demand. A sensing circuit senses ventricular activity of the heart responsive to a plurality of sensing parameters including post-pace sensing parameters and a processor adjusts the post-pace sensing parameters responsive to the selected pacing rate.

23 Claims, 5 Drawing Sheets

| Pacing Rate/CL | Decay Delay (Count) | Start Threshold |
|---|---|---|
| 150/400 | 0 (0) | 1.0 |
| 140/429 | 0 (0) | 1.1 |
| 130/462 | 0 (0) | 1.2 |
| 120/500 | 0 (0) | 1.4 |
| 110/545 | 0 (0) | 1.5 |
| 100/600 | 62.4 (2) | 1.5 |
| 90/667 | 93.6 (3) | 1.6 |
| 80/750 | 156 (5) | 1.6 |
| 60/1000 | 187.2 (6) | 1.6 |
| 30/2000 | 218.4 (7) | 1.6 |

IMPLANTABLE CARDIAC STIMULATION DEVICE AND METHOD FOR OPTIMIZING SENSING PERFORMANCE DURING RATE ADAPTIVE BRADYCARDIA PACING

This application claims the benefit of U.S. Provisional Application No. 60/172,389, filed Dec. 17, 1999.

FIELD OF THE INVENTION

The present invention generally relates to an implantable cardiac stimulation device including both a ventricular defibrillator and a rate adaptable cardiac pacemaker. The present invention more particularly relates to such a device and method providing enhanced post-pacing sensing performance.

BACKGROUND OF THE INVENTION

Combined implantable ventricular defibrillator and pacemaker stimulation devices are well known in the art. Such devices permit a heart to be paced for treating bradycardia, for example, while also detecting for ventricular fibrillation and ventricular tachycardia and applying defibrillating electrical energy, cardioversion shocks or antitachycardia pacing pulses to the heart when fibrillation or tachycardia is detected.

One problem that must be addressed in such devices is the need to provide relatively low threshold, i.e., high sensitivity, ventricular sensing for detecting fibrillation while pacing the heart. The sensing threshold must be low enough (sensitive enough) for detecting the low amplitude electrical activity of the heart during fibrillation while avoiding over-sensing which could result in a T wave being detected by the pacemaker and thus mistaken for an R wave. The foregoing is most notably a problem after a pacing stimulation pulse is applied to the heart by such devices.

In the prior art, post-pacing sensing has been performed by first establishing a ventricular refractory period (VREF) when the pacing stimulation pulse is applied and continuing the VREF for a pre-determined time through the evoked response. Following the VREF, the sensing threshold is set at an initial level, held at the initial level for a delay time, and then decreased thereafter from the initial threshold level to a minimum threshold level where it is held until the next paced or sensed event. The initial threshold, delay time and threshold decay rate are selected so that the threshold is above the amplitude of the T wave when the T wave occurs.

These post-pace sensing parameters can be varied to achieve the desired sensing threshold characteristics. For increased sensitivity to low level signals, as occur during fibrillation, it is desirable for the threshold to decrease to the minimum threshold as quickly as possible before the next pace pulse. However, to prevent over-sensing of larger T waves, particularly in patients with longer QT intervals, it is desirable for the sensing threshold to be higher or less sensitive. Therefore, the most optimal set of post-pace sensing parameters is the one which achieves the desired threshold level without over-sensing T waves. This problem is further complicated when rate adaptive pacing is implemented. Rate adaptive pacing is used with patients whose heart rates do not naturally increase in response to exercise (chronotropic incompetence). The rate adaptive pacer senses a physiologic parameter indicative of exercise and provides a corresponding increase in the pacing rate. However, this reduces the time between stimulation pulses and thus the time during which the sensing threshold can decrease to ensure the detection of low-level fibrillation signals. The time between pacing pulses is also shortened in a P-wave tracking mode for those patients whose hearts are not chronotropically incompetent. P-waves are sensed in the atria and the ventricle(s) is paced at the rate which tracks the P-waves and thus at a rate that may increase as a result of exercise or excitement. As used herein, the term "rate adaptive" is intended to include pacing at a rate that varies in response to some change in physiological condition whether that be P-wave tracking, response to a sensor measuring exercise or otherwise. Further, since the QT interval generally shortens with faster pacing rates (and conversely lengthens with slower rates), a single post-pace sensing parameter set cannot yield the most optimal thresholding for all pacing rates. Another complicating factor is the variability of QT intervals and T wave amplitudes between patients and differing conditions. Prior art sensing systems have not addressed this problem of faster pacing rates in a rate adaptive pacer reducing the amount of time available for the threshold to decrease, compounding the problem of achieving the desired threshold (or sensitivity) by the next pace pulse.

The present invention addresses the problem of achieving the optimal thresholding during variable pacing rates. The present invention achieves the optimal thresholding without requiring complicated programming of the device by the patient's physician.

SUMMARY OF THE INVENTION

The invention provides an implantable stimulation device including a ventricular defibrillator and a rate adaptive cardiac pacer which optimizes sensing performance following application of pacing pulses to a heart. The device includes a pulse generator that applies pacing stimulation pulses to a patient's heart at a stimulation rate that is a function of physiologic demand. The device further includes a sensing circuit that senses ventricular activity of the heart for supporting pacing of the heart and fibrillation detection. The sensing circuit senses ventricular activity in accordance with a plurality of sensing parameters including post-stimulation sensing parameters. The device further includes a processor that adjusts the post-stimulation sensing parameters responsive to the stimulation rate.

The invention still further provides a method of applying stimulation pulses to a heart and sensing ventricular activity after applying a stimulation pulse to the heart. The method includes the steps of applying stimulation pulses to a heart at a stimulation rate that is a function of physiologic demand, sensing ventricular activity of the heart responsive to a plurality of sensing parameters including post-stimulation sensing parameters, and adjusting the post-stimulation sensing parameters responsive to the calculated stimulation rate.

BRIEF DESCRIPTION OF THE DRAWINGS

The above and other aspects, features and advantages of the present invention will be more apparent from the following more particular description thereof, presented in conjunction with the following drawings and wherein.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
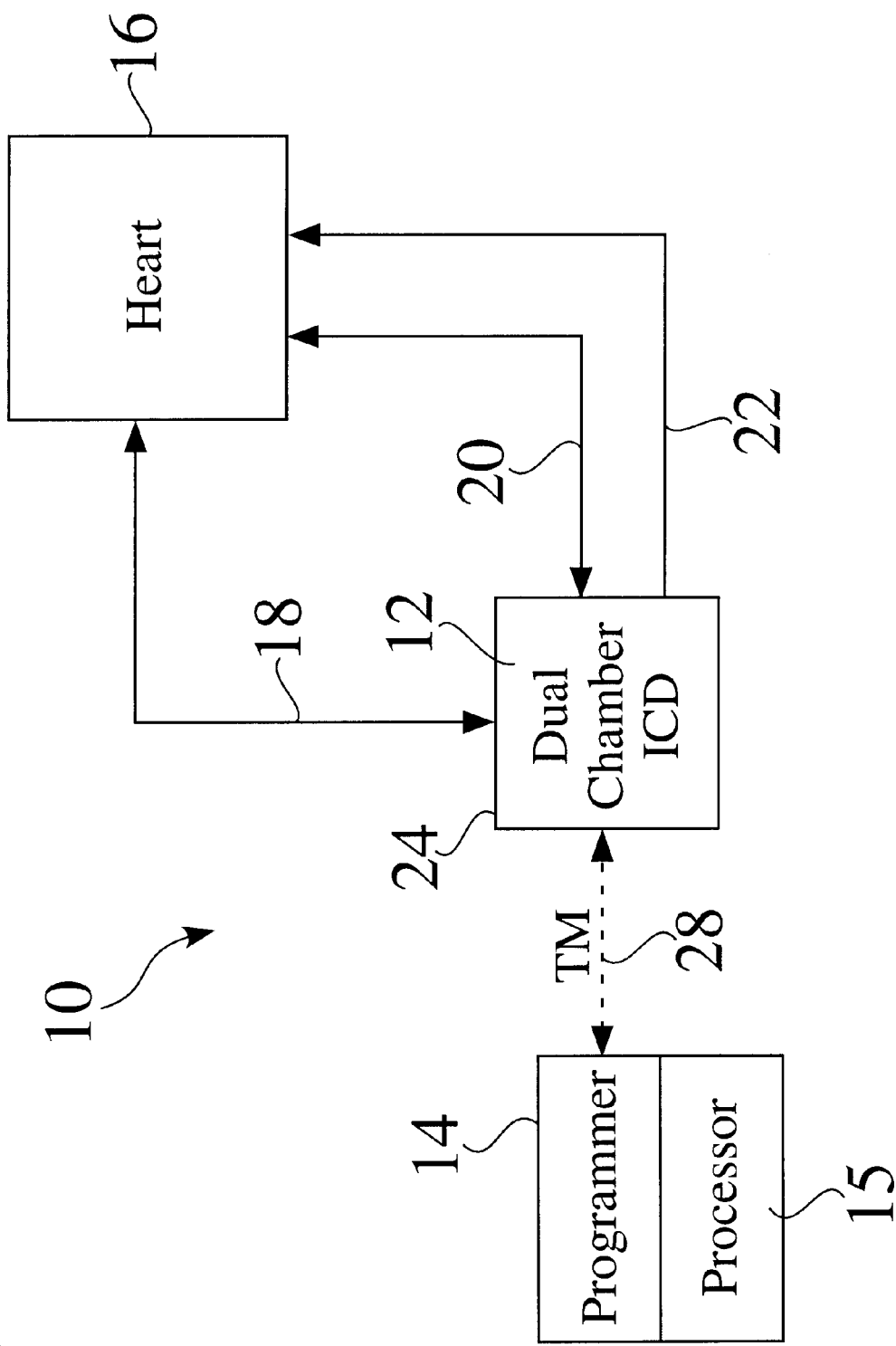
FIG. 1 shows a simplified functional block diagram illustrating an implantable cardiac stimulation system in which the present invention may be used.

Referring now to FIG. 1, the implantable cardiac stimulation system 10 there illustrated includes a dual chamber implantable cardioverter-defibrillator (ICD) 12 and an external programmer 14. The ICD is preferably of the type that includes both a cardioverter/defibrillator and a rate adaptive pacemaker. The pacemaker may be, in accordance with the present invention, either a single chamber ventricular pacemaker or a dual chamber pacemaker.

The implantable device or ICD is coupled to a patient's heart 16 by a plurality of electrode carrying leads 18, 20, and 22. The lead 18 is preferably an atrial pacing and sensing lead having a bipolar electrode pair of the type well known in the art positioned in the right atrium of the patient's heart 16 in a known manner. The lead 20 preferably is a ventricular pacing and sensing lead having a bipolar electrode pair, also of the type well known in the art, positioned in the right ventricle of the patient's heart 16. As is well known, an additional pacing and sensing lead (not shown) may be employed having a bipolar electrode pair positioned in the coronary sinus to provide left side sensing and pacing of the heart. Lastly, the lead 22 is preferably a defibrillation lead having a first or proximal shock coil electrode positioned in the superior vena cava (SVC) of the patient's heart and a second or distal shock coil electrode positioned in the right ventricle of the patient's heart as is well known in the art. In a preferred embodiment all of the conductors and electrodes are combined in a single lead or in some cases two leads with the elements of leads 20 and 22 combined.

The leads 18 and 20 support dual chamber pacing of the heart 16 and sensing of electrical activity of the right atrium and right ventricle respectively of the heart 16. Such sensing allows the dual chamber pacemaker to stimulate the right atrium and right ventricle only when necessary on demand, i.e., in the absence of a sensed intrinsic depolarization. The sensing provided by lead 20 also provides for detection of tachyarrhythmias, such as ventricular fibrillation and ventricular tachycardia of the heart 16. Lastly, the lead 22 permits defibrillation or cardioversion shocks to be applied to the heart when fibrillation or tachycardia is detected. The defibrillation shocks are preferably applied from the combination of the conductive housing 24 and the proximal shock coil in the SVC to the distal shock coil in the right ventricle. Alternatively, the lead may be provided with only one shock coil for positioning in the right ventricle. With this arrangement, the defibrillation shocks may be applied between the conductive housing 24 of the ICD 12 and the right ventricular shock coil, as is known in the art.

The ICD 12 detects activity of the heart, provides stimulation pacing pulses and/or high voltage shocks to the heart to treat tachyarrhythmias and bradycardia of the heart in accordance with a plurality of programmable parameters. The programmable parameters are provided by the programmer 14 under selective operation by the patient's physician. The programmable parameters are conveyed by the programmer 14 to the ICD 12 over a telemetry link 28 in a known manner.

The ICD 12 relies on accurate sensing to expediently detect low level fibrillation signals while at the same time avoiding over-sensing of T waves during bradycardia pacing. As will be seen hereinafter, the ICD 12 includes a sensing circuit that senses activity of the heart in accordance with a plurality of sensing parameters. In accordance with the present invention, the sensing parameters include post-pacing sensing parameters which are automatically adjusted by the ICD 12 depending on the calculated pacing stimulation rate of the rate adaptive pacer. The post-stimulation sensing parameters are preferably obtained by the ICD 12 from a look-up table residing in a static RAM memory 54 within the ICD 12 as this is more energy efficient than calculating these parameters in the ICD microprocessor. Alternatively the post-stimulation sensing parameters may be determined for each of a plurality of anticipated stimulation rate ranges by a processor 15 within programmer 14 or by a processor within the ICD 12. If the programmer determines the parameters, it loads the look-up table with the determined parameters by transmitting the parameters to the ICD 12 over the telemetry link 28.

The post-stimulation sensing parameters define the value of the post-stimulation sensing threshold used to sense ventricular activity using lead 20. As may be seen in FIG. 5, the sensing threshold is set to an initial or start value 30 at the end of a ventricular refractory period (VREF) which is imposed following the application of a pacing stimulation pulse 32. As mentioned above, VREF may be fixed or may vary as a function of the pacing rate. The R-wave feature 34 is the evoked response of the heart resulting from the stimulation pulse 32. The sensing threshold may then be held constant for a decay delay 36 depending on the calculated stimulation rate. It is noted that in the preferred embodiment the ICD microprocessor calculates during VREF when the next pacing pulse is expected to be delivered based on sensor input, P-wave tracking rate and/or other parameters. It then determines the post-stimulation sensing parameters, also within the VREF period. In an alternative embodiment, the microprocessor may adaptively determine when the next stimulation pulse is to be delivered on an on-going basis including additional parameters such as, for example, the morphology of the evoked response. The duration of the decay delay,if there is one, is further dependent on the calculated pacing rate of the rate adaptive pacer. Following the decay delay 36, the sensing threshold is decreased at a prescribed decay rate until it reaches a minimum threshold 31 prior to the time for the next stimulation pulse 38. In the preferred embodiment, the prescribed decay rate remains constant regardless of the selected stimulation rate. Other decay functions such as a step function or a parabolic decay can be used to decrease the sensing threshold.

Figures 5, 6:
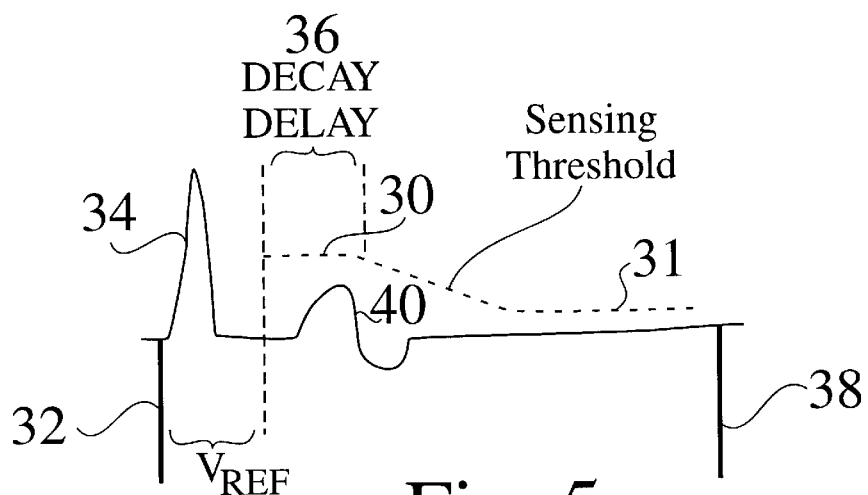
FIG. 5 is a waveform of a paced cardiac cycle illustrating particular aspects of the present invention.
FIG. 6 is a look-up table which may be used to adjust the post-pace sensing parameters in accordance with the present invention.

In accordance with the present invention, the post-stimulation sensing parameters which are adjusted to the calculated rate responsive pacing rate include the initial threshold 30 and the decay delay 36. Since the prescribed decay rate is the same for each pacing rate, by adjusting the decay delay 36 and the initial threshold 30, responsive to the pacing rate, over-sensing causing detection of a T wave may be avoided. In FIG. 5, sensing of the T wave 40 is avoided since the threshold is above the amplitude of the T wave when the T wave occurs.

FIG. 6 shows an illustrative look-up Table 42. The look-up Table 42 preferably resides within a memory within the ICD 12. As will be noted, for each pacing rate range, the look-up Table 42 defines a value of a decay delay and start threshold. As previously mentioned, the look-up Table 42 may not call for a decay delay at some pacing rates. The reason for this is that at higher pacing rates, the QT interval may be short enough so that the T-wave falls within VREF. This renders a decay delay to be unnecessary. A manner of determining the look-up table parameters will be described subsequently. In an alternative embodiment (not shown) the look-up table may include other variable post-stimulation sensing parameters such as a variable VREF or a variable decay rate. Further, the start threshold in the look-up table is used in the case of a paced event. In the case of a sensed event, the pulse generator determines the maximum amplitude signal detected during VREF. Upon expiration of VREF, the sensing threshold is set to a programmed percentage of the detected maximum amplitude.

Figure 2:
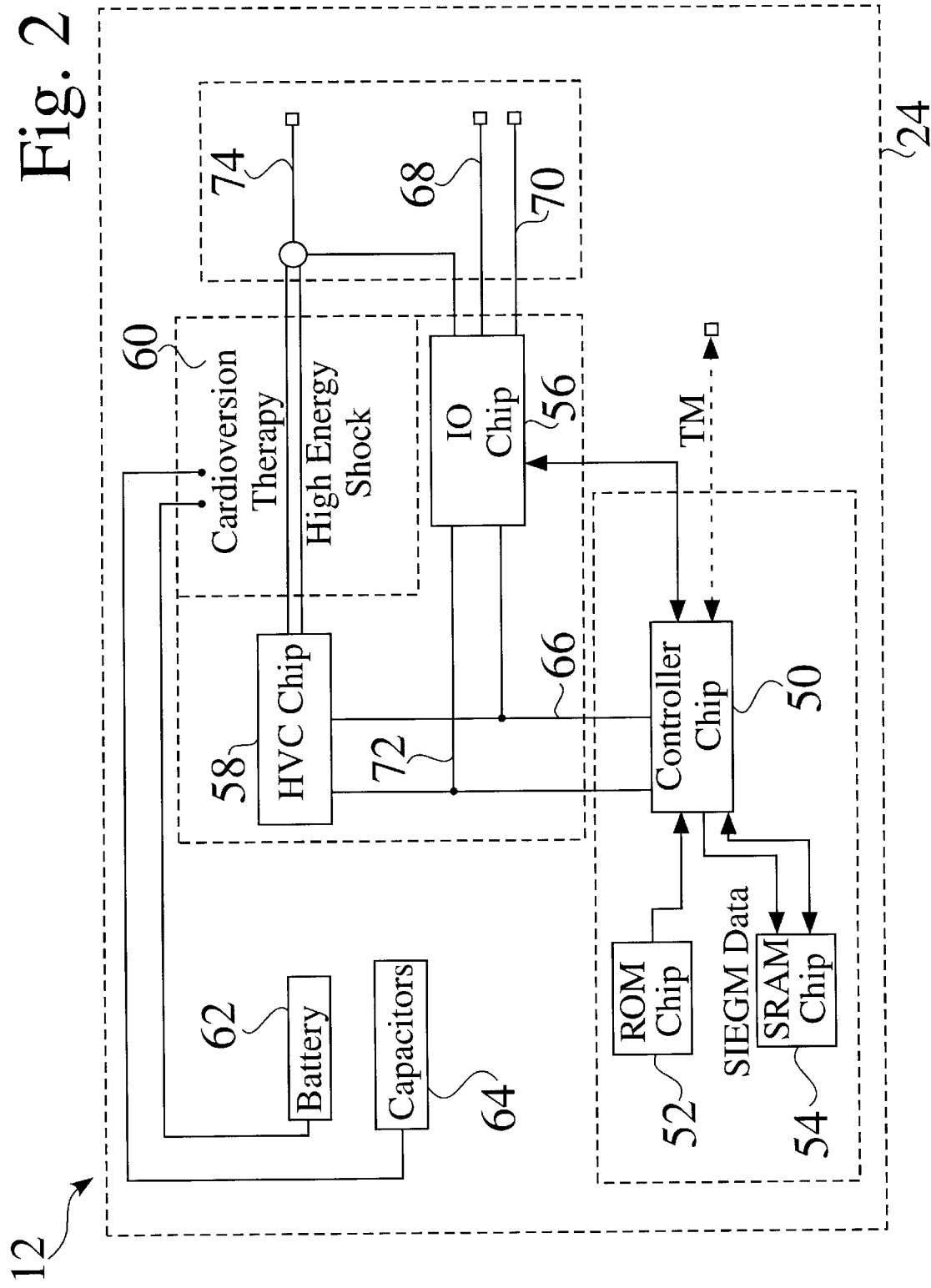
FIG. 2 shows a functional block diagram of an implantable combined cardioverter/defibrillator and pacemaker device embodying the present invention.

Referring now to FIG. 2, the ICD 12 includes within the electrically conductive housing 24 a controller chip 50, a read-only memory (ROM) chip 52, a static random access memory (SRAM) chip 54, and an IO chip 56. The ICD 12 further includes a high voltage controller (HVC) chip 58, and high voltage output stage 60, a battery 62, and high voltage capacitors 64.

The above-mentioned chips form an ICD hybrid. The hybrid is connected through a system of address and data buses 66 forming a highly specialized, computerized, embedded system.

The controller 50, to be described in greater detail subsequently, provides the main control of the ICD 12 and determines its functionality. The controller 50 is coupled to the ROM 52 which contains the software of the ICD 12. This software includes operating instructions which the controller 50 executes to control the operation of the ICD 12.

The SRAM 54 may contain the aforementioned look-up table defining the adjustable post-pace sensing parameters and the programmable parameters of the ICD 12. It also preferably includes buffers for a stored intracardiac electrogram (SIEGM) subsystem.

The IO chip 56 regulates the sensing function of the ICD 12. To this end, it receives over the address and data buses 66 the sensing parameters including the post-pace sensing parameters. The 10 chip provides trigger pulses over a bus 68 which causes delivery of pacing stimulus pulses to the heart. It further receives electrogram signals from the atrial and ventricular leads 18 and 20 respectively over another bus 70. When the 10 chip detects a cardiac event within the right atrium or right ventricle, it generates an interrupt on a bus 72. The interrupts are used for timing and diagnostic purposes.

The HVC chip 58 controls the high voltage output stage 60. It receives data from the controller 50 over buses 66 defining the magnitude of electrical energy to be delivered to the heart for cardioversion and defibrillation therapy. It further receives interrupts from the 10 chip 56 over bus 72 to control the timing of therapy delivery.

The high voltage output stage 60 is coupled to the battery 62 and the HV capacitors 64. It includes DC-to-DC converter circuitry which convert the DC battery voltage to a relatively high voltage for charging the high voltage capacitors 64. Under control of the HVC chip 58, the high voltage output stage 60 discharges the capacitors into the heart for terminating detected tachyarrhythmias. The cardioversion/ defibrillation energy is applied to lead 22 over a conductor 74.

Figure 3:
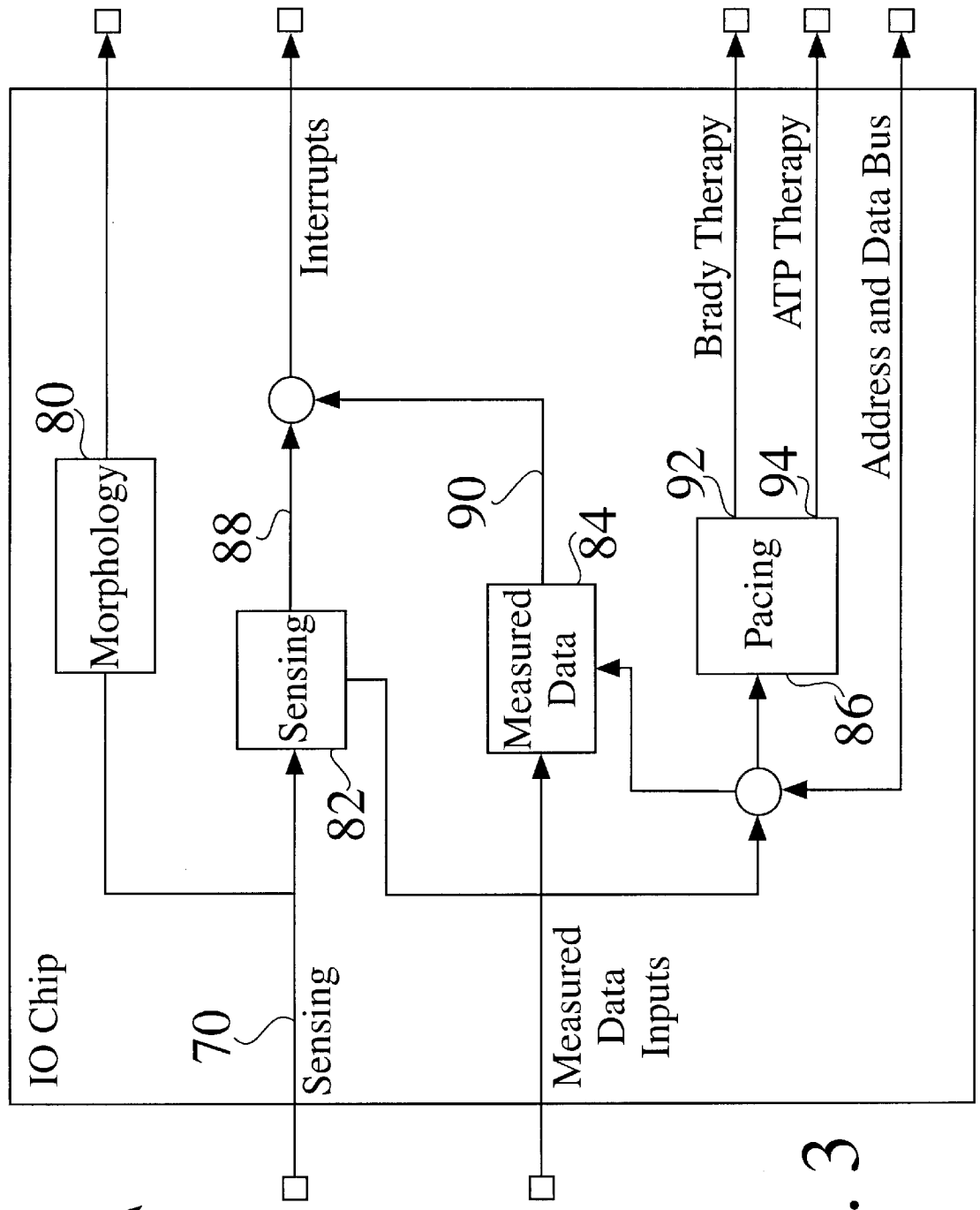
FIG. 3 shows a functional block diagram of the 10 chip of the device of FIG. 2.

As previously mentioned, the IO chip 56 regulates the sensing function of the ICD 12. The IO chip 56 is shown in greater detail in FIG. 3. The IO chip 56 generally includes a morphology stage 80, a sensing stage 82, a measured data stage 84 and a pacing stage 86.

The morphology stage 80 and sensing stage 82 receive a common input over buses 70 from the atrial and ventricular leads 18 and 20 respectively (FIG. 1). The morphology stage 80 analyzes the electrogram signals to help distinguish supraventricular tachycardias from ventricular tachycardias.

The sensing stage 82 includes sense amplifiers (not shown) of the type well known in the art for amplifying and filtering the raw electrogram signals. One of the sense amplifiers is a ventricular sense amplifier whose sensitivity or threshold is controlled by the controller 50 (FIG. 2) which uses the sensing parameters, including the post-pacing sense parameters, contained in the look-up table stored in the SRAM 54. When the sensing stage 82 detects an R wave, it provides an interrupt on conductor 88. The interrupt notifies the controller chip 50 (FIG. 2) of intrinsic activity. The frequency of the interrupts are utilized by the controller to determine if antibradycardia, antitachycardia, or defibrillation therapy is necessary.

The measured data stage 84 performs measurements of various ICD parameters. These parameters include the voltage of the battery 62, the voltage on capacitors 64, the lead impedance of the defibrillation lead 22 (FIG. 1) and the lead impedance of the atrial and ventricular sense/pace leads 18 and 20 respectively (FIG. 1). The measured data stage provides an interrupt over line 90 to notify the controller 50 when a measurement has been completed.

The pacing stage 86 generates stimulation pulses for bradycardia therapy at an output 92 and antitachycardia pacing therapy at an output 94. The sensing stage 82 is coupled to the pacing stage 86 to cause the pacing stage 86 to generate stimulation pacing pulses only in the absence of intrinsic activity. The pacing stage 86 generates stimulation pacing pulses having a specified amplitude and width as controlled by the controller 50.

Figure 4:
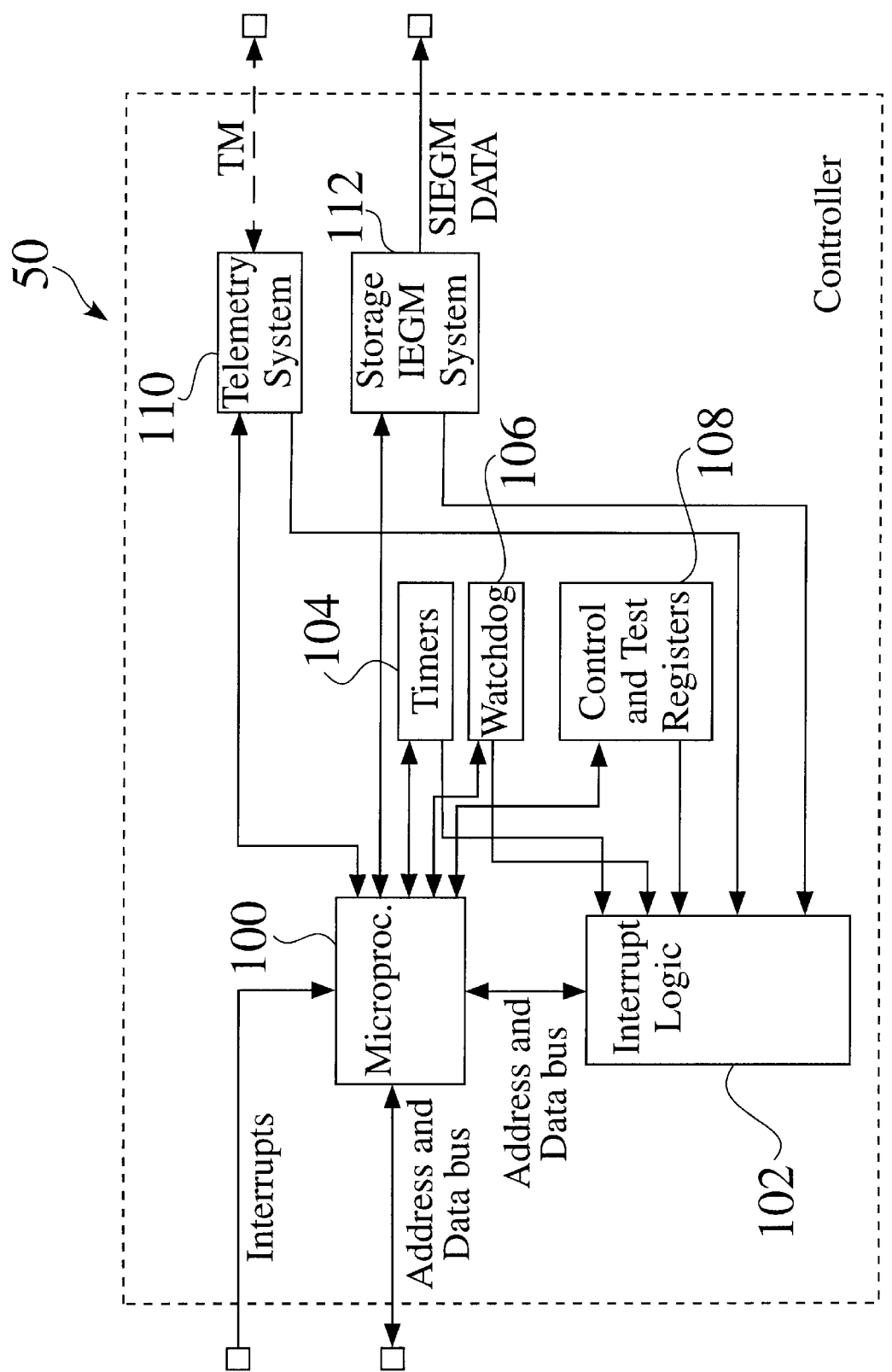
FIG. 4 shows a functional block diagram of the controller of the device of FIG. 2.

FIG. 4 is a more detailed block diagram of the controller 50. The controller 50 includes a processor 100, interrupt logic 102, timers 104, a watchdog subsystem 106, and control and test registers 108. The controller 50 further includes a telemetry circuit or system 110 and an IEGM storage system 112.

The processor 100 is the main component of the controller 50. It and the other subsystems identified above facilitate the implementation of the ICD functions.

Telemetry circuit 110 is configured to provide full duplex communication with the external programmer 14 (FIG. 1). It provides bidirectional data paths for downloading programmable parameters, including post-pacing sensing parameters in accordance with the present invention, and instructions to the ICD 12 (FIG. 1). In accordance with one aspect of the present invention, the programmer 14 may determine the post-pacing sensing parameters and transmit them to the ICD 12 via the telemetry circuit 110, for storage by the processor 100 in the look-up table of the SRAM 54 (FIG. 2). Alternatively, the processor 100 may determine the post-pacing sensing parameters for storage in the look-up table of SRAM 54 after receiving predicted factors for QT interval prediction from the programmer via the telemetry circuit 110. The telemetry circuit 110 further permits the programmer to interrogate the ICD to determine status information and to retrieve the SIEGM stored in the IEGM storage system 112. The pacing rate in the look-up table 42 is also programmable.

The IEGM storage system 112 consists of SRAM chips where the digitized IEGM is stored as is disclosed in U.S. Pat. No. 5,732,708 which is incorporated herein by reference. The stored data may be transferred to the programmer through the telemetry circuit 110 for further analysis.

The timers 104 provide accurate time measurements and event processing. The timers 104 interrupt the processor 100 when they expire and require processor service.

The watchdog subsystem 106 provides a safety mechanism against runaway software processes. For example, if the processor 100 is held in an infinite loop, the watchdog system will cause a system wide reset to occur.

The control and test registers 108 allow various software processes to change the hardware configuration by changing the contents of programmable registers. Interrupts may be enabled, disabled or acknowledge by using registers within the control and test registers 108.

The pacing rate dependent post-pace sensing parameters may be calculated based upon the alert period, the predicted QT interval at that rate, the maximum T wave amplitude anticipated and the threshold level desired before the next pacing pulse is delivered. More specifically, the following equations may be implemented by either the processor 15 of the programmer 14 (FIG. 1) or the processor 100 (FIG. 4) of the ICD 12 to determine the rate dependent post-pace sensing parameters.

$$\text{Predicted QT} = \text{QT\_Scaling\_Factor} * \text{Pacing Rate Bin}^{-exp} \quad \text{Eqn.(1)}$$

Where QT_Scaling_Factor=9609.7 and exp=0.7056

$$\text{Start Threshold} = \text{Truncate}((\text{Cycle length of Rate Bin} - \text{VREF}) * (0.05/15.6) + \text{Max Sens}) \quad \text{Eqn. (2)}$$

Where Max Sens=0.6

$$\text{Decay delay} = (\text{Predicted QT} - \text{VREF}) - (\text{Start threshold} - \text{T wave}) * (15.6/0.05) \quad \text{Eqn. (3)}$$

Where

For a Pacing Rate Bin of 130 to 150, T wave=1.0

For a Pacing Rate Bin of 110 to 120, T wave=1.15

For a Pacing Rate Bin of 100, T wave=1.3

For a Pacing Rate Bin of 90, T wave=1.4

For a Pacing Rate Bin of 30 to 80, T wave=1.5

With respect to equation 2, for a Pacing Rate Bin of 100 to 150, if calculated start threshold is greater than 1.5, the start threshold is set equal to 1.5. For a Pacing Rate Bin of 30 to 90, if the calculated start threshold is greater than 1.6, start threshold is set equal to 1.6. If the calculated start threshold is less than 0.9, the start threshold is set equal to 0.9. Further, the following conditions have precedence over the calculated decay delay: i. If predicted QT is less than VREF, then the predicted QT interval is within refractory and decay delay 0. ii. If start threshold is less than T Wave, then the decay delay=0. iii. If the pacing rate is 150, then the decay delay=0.

The alert period, predicted QT intervals, maximum T wave amplitudes anticipated, and the threshold level desired before the next pace pulse may be prestored for use in determining the rate dependent post-pace sensing parameters. Alternatively, and in accordance with the present invention, the determination process may be customized by a user if oversensing of T waves is experienced or if there is a desire to increase sensing sensitivity. In accordance with this aspect of the present invention, the user may select via the programmer the T wave amplitude, QT interval, and pacing rate with which oversensing is observed to determine the rate dependent post-pace sensing parameters using the relationships given above. Either the programmer or the ICD will then recalculate the appropriate parameters to prevent oversensing and to achieve the desired sensitivity before the next pacing pulse is to be delivered. This method of inputting clinical parameters to modify the sensing threshold behavior is more intuitive to the user as compared to directly changing the post-pace sensing parameters.

While the invention herein disclosed has been described by means of specific embodiments and applications thereof, numerous modifications and variations could be made thereto by those skilled in the art without departing from the scope of the invention set forth in the claims.

What is claimed is:

1. An implantable cardiac stimulation device including a ventricular defibrillator and a rate adaptive cardiac pacer comprising:

pulse generating means for applying stimulation pulses to a patient's heart at a variable stimulation rate that is a function of a sensed physiologic demand;

sensing means for sensing ventricular activity of the heart responsive to a plurality of sensing parameters including post-stimulation sensing parameters including an initial sensing threshold; and adjusting means for adjusting the initial sensing threshold responsive to a calculated stimulation rate.

2. The device of claim 1 further including processing means for determining the post-stimulation sensing parameters responsive to the calculated stimulation rate.

3. The device of claim 1 wherein the device includes a look-up table including the post-stimulation sensing parameters versus stimulation rate for adjusting the post-stimulation sensing parameters responsive to the calculated stimulation rate.

4. The device of claim 3 further including processing means for providing the look-up table with the post-stimulation sensing parameters versus stimulation rate.

5. The device of claim 4 wherein the processing means provides the look-up table with the post-stimulation sensing parameters versus stimulation rate based upon fixed criteria.

6. The device of claim 4 wherein the processing means provides the look-up table with the post-stimulation sensing parameters versus stimulation rate based upon selectable criteria.

7. An implantable cardiac stimulation device including a ventricular defibrillator and a cardiac pacer comprising:

a pulse generator that applies stimulation pulses to a heart at a variable stimulation rate;

a sensing circuit that senses ventricular activity of the heart responsive to a plurality of sensing parameters including post-stimulation sensing parameters;

a processor that adjusts the post-stimulation sensing parameters responsive to a calculated stimulation rate; and wherein the sensing circuit has an initial sensing threshold, wherein the initial sensing threshold is one of the post-stimulation sensing parameters and wherein the processor adjusts the initial sensing threshold responsive to the calculated stimulation rate.

8. The device of claim 7 wherein the processor is programmed to determine the post-stimulation sensing parameters responsive to the calculated stimulation rate.

9. The device of claim 7 further including a memory having a look-up table including the post-stimulation sensing parameters versus stimulation rate.

10. The device of claim 9 wherein the processor is programmed to provide the look-up table with the post-stimulation sensing parameters versus stimulation rate.

11. The device of claim 10 wherein the processor is programmed to provide the look-up table with the post-stimulation sensing parameters versus stimulation rate based upon fixed criteria.

12. The device of claim 11 wherein the processor is programmed to provide the look-up table with the post-stimulation sensing parameters versus stimulation rate based upon selectable criteria.

13. In an implantable stimulation device including a ventricular defibrillator and a rate adaptive cardiac pacer, a method of applying stimulation pulses to a heart and sensing ventricular activity after applying a stimulation pulse including the steps of:

applying stimulation pulses to a heart at a stimulation rate that varies as a function of physiologic demand;

sensing ventricular activity of the heart responsive to a plurality of sensing parameters including post-stimulation sensing parameters; and adjusting one of the post-stimulation sensing parameters comprising an initial sensing threshold responsive to a calculated stimulation rate.

14. The method of claim 13 wherein one of the post-stimulation sensing parameters is an initial sensing threshold and wherein the adjusting step includes adjusting the initial sensing threshold responsive to the calculated stimulation rate.

15. The method of claim 13 wherein the sensing step includes decreasing a sensing threshold a delay time after applying a stimulation pulse, wherein the delay time is one of the post-stimulation sensing parameters, and wherein the adjusting step includes adjusting the delay time responsive to the calculated stimulation rate.

16. The method of claim 13 further including the step of determining the post-stimulation sensing parameters prior to calculating the selected stimulation rate.

17. The method of claim 13 including the further step of providing a look-up table including the post-stimulation sensing parameters versus stimulation rate and wherein the adjusting step includes obtaining the post-stimulation sensing parameters from the look-up table responsive to the calculated stimulation rate.

18. The method of claim 17 including the further step of providing the look-up table with the post-stimulation sensing parameters versus stimulation rate.

19. The method of claim 18 wherein the step of providing the look-up table with the post-stimulation sensing parameters versus stimulation rate is performed based upon fixed criteria.

20. The method of claim 18 wherein the step of providing the look-up table with the post-stimulation sensing parameters versus stimulation rate is performed based upon selectable criteria.

21. An implantable cardiac stimulation device including a ventricular defibrillator and a rate adaptive cardiac pacer comprising:

pulse generating means for applying stimulation pulses to a patient's heart at a variable stimulation rate that is a function of a sensed physiologic demand;

sensing means for sensing ventricular activity of the heart responsive to a plurality of sensing parameters including post-stimulation sensing parameters including a decreasing sensing threshold which begins decreasing a delay time after application of a stimulation pulse; and adjusting means for adjusting the delay time responsive to the calculated stimulation rate.

22. An implantable cardiac stimulation device including a ventricular defibrillator and a cardiac pacer comprising:

a pulse generator that applies stimulation pulses to a heart at a variable stimulation rate;

a sensing circuit that senses ventricular activity of the heart responsive to a plurality of sensing parameters including post-stimulation sensing parameters;

a processor that adjusts the post-stimulation sensing parameters responsive to a calculated stimulation rate; and wherein the sensing circuit has a decreasing sensing threshold which begins decreasing a delay time after application of a stimulation pulse, wherein the delay time is one of the post-stimulation sensing parameters, and wherein the process adjusts the delay time responsive to the calculated stimulation rate.

23. In an implantable stimulation device including a ventricular defibrillator and a rate adaptive cardiac pacer, a method of applying stimulation pulses to a heart and sensing ventricular activity after applying a stimulation pulse including the steps of:

applying stimulation pulses to a heart at a stimulation rate that varies as a function of physiologic demand;

sensing ventricular activity of the heart by setting a sensing threshold and decreasing the sensing threshold a delay time after applying a stimulation pulse; and adjusting the delay time responsive to a calculated stimulation rate.

* * * * *